(12) United States Patent
Chiesi et al.

(10) Patent No.: US 9,121,727 B2
(45) Date of Patent: Sep. 1, 2015

(54) LOW-ENERGY-CONSUMPTION TEMPERATURE COMPENSATION FOR A DETECTION SYSTEM

(75) Inventors: Laurent Chiesi, Reaumont (FR); Hynek Raisigel, Sassenage (FR); Gilles Chabanis, Grenoble (FR)

(73) Assignee: Schneider Electric Industries SAS, Rueil Malmaison (FR)

( * ) Notice: Subject to any disclaimer, the term of this patent is extended or adjusted under 35 U.S.C. 154(b) by 585 days.

(21) Appl. No.: 13/478,297

(22) Filed: May 23, 2012

(65) Prior Publication Data
US 2013/0001397 A1    Jan. 3, 2013

(30) Foreign Application Priority Data
Jun. 29, 2011 (FR) ..................... 11 55790

(51) Int. Cl.
*H01J 40/14* (2006.01)
*G01D 3/036* (2006.01)
*G01D 5/34* (2006.01)

(52) U.S. Cl.
CPC ............. *G01D 3/036* (2013.01); *G01D 5/34* (2013.01); *G01N 2201/0624* (2013.01)

(58) Field of Classification Search
CPC ......... G01D 5/34; G01J 1/4204; G01J 1/4228
USPC ........... 250/214 R, 214.1, 238, 205; 315/308, 315/307, 256; 327/515, 514
See application file for complete search history.

(56) References Cited

U.S. PATENT DOCUMENTS

| 5,165,380 | A | 11/1992 | Okamura |
| 6,356,774 | B1 | 3/2002 | Bernstein et al. |
| 6,574,425 | B1 | 6/2003 | Weiss et al. |
| 8,649,012 | B2 * | 2/2014 | Beckmann et al. ........... 356/437 |
| 2003/0214655 | A1 | 11/2003 | Weiss et al. |

OTHER PUBLICATIONS

French Preliminary Search Report and Written Opinion issued Feb. 13, 2012, in French 1155790, filed Jun. 29, 2011 (with English Translation of Categories of Cited Documents).

* cited by examiner

*Primary Examiner* — Que T Le
(74) *Attorney, Agent, or Firm* — Oblon, McClelland, Maier & Neustadt, L.L.P.

(57) ABSTRACT

A detection system that includes an emitter, a power supply source, a receiver, a detector, and a processor. The emitter includes a light-emitting diode that emits a luminous signal. The power supply source applies a constant voltage to the light-emitting diode. The receiver senses the luminous signal emitted by the light-emitting diode and generates a first input signal representative of the luminous signal detected. The detector measures the current passing through the light-emitting diode and generates a second input signal representative of the current measured. The processor is connected to the receiver and provides an output signal as a function of the first input signal and of the second input signal.

4 Claims, 1 Drawing Sheet

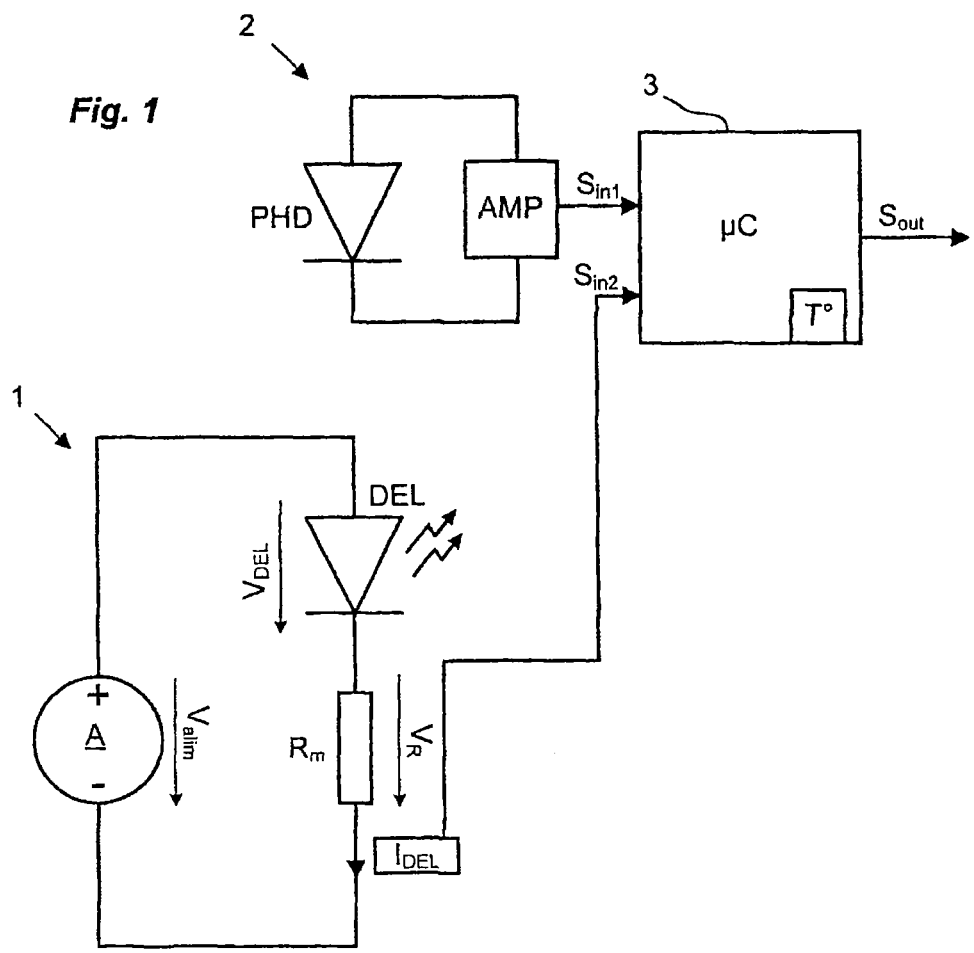
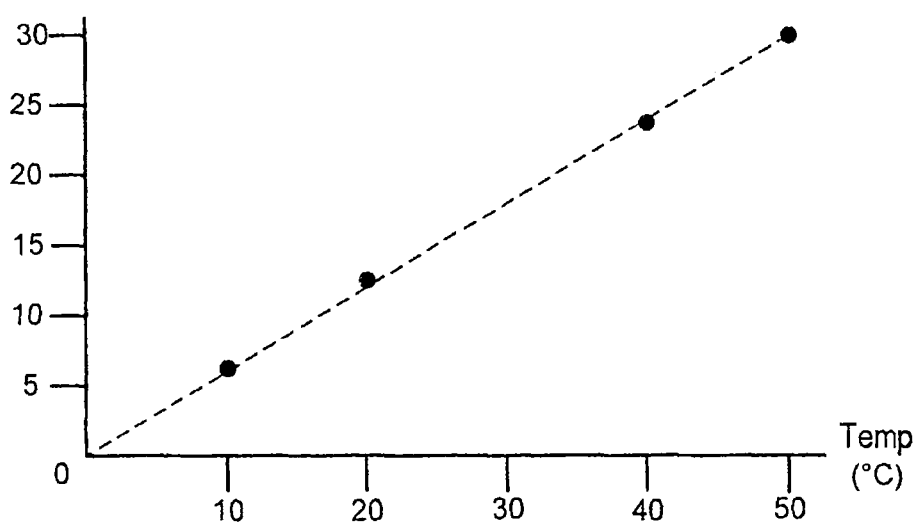

LOW-ENERGY-CONSUMPTION TEMPERATURE COMPENSATION FOR A DETECTION SYSTEM

TECHNICAL FIELD OF THE INVENTION

The present invention pertains to a detection system comprising an emitter able to emit a luminous signal, a receiver of the luminous signal and processing means. The invention will in particular be perfectly suitable for determining the concentration of a gas of carbon dioxide type.

PRIOR ART

When a detection system employs a light-emitting diode as emitter, it is known that it must comprise means making it possible to limit or to compensate for the effect of the temperature on the luminous signal emitted by the light-emitting diode. As a general rule, these means make it possible to vary the level of current injected into the light-emitting diode so as to maintain its optical power at a nearly constant value whatever the temperature of the light-emitting diode. By requiring permanent action on the current injected into the light-emitting diode, these solutions do not foster low energy consumption.

The aim of the invention is to propose a detection system making it possible to compensate for part of the temperature-related effect on the detection performed while exhibiting low energy consumption and not degrading the signal-noise ratio.

DISCLOSURE OF THE INVENTION

This aim is achieved by a detection system comprising:
an emitter comprising a light-emitting diode able to emit a luminous signal and a power supply source designed to power the light-emitting diode,
a receiver intended to sense the luminous signal emitted by the light-emitting diode and designed to generate a first input signal representative of the luminous signal detected,
processing means connected to the receiver to provide an output signal,
the system being characterized in that:
the power supply source is a voltage source designed to apply a constant voltage to the light-emitting diode,
the system comprises means for measuring the current passing through the light-emitting diode and intended to generate a second input signal representative of the current measured,
the processing means comprise means for determining the output signal as a function of the first input signal and of the second input signal.

According to a particular feature, the processing means comprise a microcontroller storing temperature calibration parameters employed to determine the output signal on the basis of the first input signal and of the second input signal.

According to another particular feature, the measurement means comprise a measurement resistor connected in series with the light-emitting diode.

According to another particular feature, the receiver comprises a photodiode and a current amplifier which are configured to generate the first input signal.

BRIEF DESCRIPTION OF THE FIGURES

Other characteristics and advantages will become apparent in the detailed description which follows offered with regard to the appended drawings in which:

FIG. 1 represents the basic diagram of the detection system of the invention,

FIG. 2 represents the curve of the increase in the current passing through the light-emitting diode (in %) as a function of measured temperature (Temp) (in ° C.).

DETAILED DESCRIPTION OF AT LEAST ONE EMBODIMENT

The invention relates to a detection system intended in particular for determining the concentration of a gas, such as for example carbon dioxide. The detection system of the invention exhibits the advantage of consuming very little energy during each measurement and of not degrading the signal-noise ratio.

With reference to FIG. 1, the detection system of the invention comprises an emitter 1 comprising a light-emitting diode (DEL) able to emit a luminous signal and a power supply source A to which the light-emitting diode DEL is connected. The power supply source A consists of a voltage source delivering a constant voltage $V_{alim}$ so as to be able to apply a constant voltage $V_{DEL}$ to the light-emitting diode DEL. With a constant voltage $V_{DEL}$ across the terminals of the light-emitting diode DEL, the current $I_{DEL}$ which passes through the diode evolves substantially with temperature since the forward bias voltage of the light-emitting diode DEL varies inversely with temperature. Consequently, at constant voltage, the current which passes through the light-emitting diode DEL increases in a quasi-linear manner as the temperature increases. The curve represented in FIG. 2 makes it possible to illustrate this phenomenon.

The detection system of the invention also comprises a receiver 2 which is distant with respect to the emitter 1 and comprising for example a photodiode (PHD) intended to sense the luminous signals emitted by the emitter 1 and a current amplifier AMP making it possible to transform the electrical current generated by virtue of the photodiode PHD into a first input signal $S_{in1}$ utilizable downstream by processing means 3. The gas to be detected is typically placed between the emitter 1 and the receiver 2.

As the light-emitting diode DEL is powered by a constant voltage source, the detection system also comprises means for measuring the current $I_{DEL}$ passing through the light-emitting diode DEL. The variation in the measured current $I_{DEL}$ is representative of the variation in the temperature influencing the optical power of the light-emitting diode DEL. The measurement means comprise for example a measurement resistor $R_m$ connected in series with the light-emitting diode DEL, whose voltage $V_R$ is monitored by the processing means 3 with a view to deducing therefrom the current $I_{DEL}$ passing through the light-emitting diode DEL. In FIG. 1, the current $I_{DEL}$ is represented by a second input signal $S_{in2}$ applied to the processing means 3.

The first input signal $S_{in1}$ and the second input signal $S_{in2}$ are for example transformed into digital signals by analogue-digital converters implemented in the processing means 3. The processing means 3 comprise a microcontroller μC intended to process the two digital signals obtained so as to determine an output signal $S_{out}$ representative of the state of detection. The processing consists in determining an output voltage, corresponding to the concentration of the gas to be measured, on the basis of the first input signal $S_{in1}$, of the second input signal $S_{in2}$ and of temperature calibration parameters (T°) initially stored in the microcontroller μC. These calibration parameters T° are for example stored in a memory of the microcontroller μC and are applied to the second input signal $S_{in2}$ so as to take account of the influence of the temperature in the determination of the output signal $S_{out}$.

Moreover, since the light-emitting diode DEL is powered voltage-wise, as the temperature increases, the optical power of the diode DEL at constant current decreases and therefore the signal-noise ratio SNR decreases. Now, when the diode DEL is powered by a constant voltage, its current increases as the temperature increases. Consequently, the loss of optical power is limited, as is the degradation in the signal-noise ratio SNR.

The invention claimed is:

1. Detection system comprising:
    an emitter comprising a light-emitting diode to emit a luminous signal and a power supply source to power the light-emitting diode,
    a receiver to sense the luminous signal emitted by the light-emitting diode and to generate a first input signal representative of the luminous signal detected, and
    a processor connected to the receiver to provide an output signal,
    the system being characterized in that:
    the power supply source is a voltage source designed to apply a constant voltage to the light-emitting diode,
    the system comprises a detector to measure the current ($I_{DEL}$) passing through the light-emitting diode (DEL) and to generate a second input signal ($S_{in2}$) representative of the current ($I_{DEL}$) measured, and
    the processor determines the output signal as a function of the first input signal and of the second input signal.

2. Detection system according to claim 1, characterized in that the processor comprises a microcontroller storing temperature calibration parameters employed to determine the output signal on the basis of the first input signal and of the second input signal.

3. Detection system according to claim 1, characterized in that the detector comprises a measurement resistor connected in series with the light-emitting diode.

4. Detection system according to claim 1, characterized in that the receiver comprises a photodiode and a current amplifier which are configured to generate the first input signal.

* * * * *